US007938812B2

(12) United States Patent
Moberg-Alehammar et al.

(10) Patent No.: US 7,938,812 B2
(45) Date of Patent: May 10, 2011

(54) INSERT FOR AN ABSORBENT ARTICLE WITH SKINCARE AGENT AND SPACING SHEET

(75) Inventors: Barbro Moberg-Alehammar, Mölndal (SE); Bo Runeman, Jonsered (SE); Ingemar Fernfors, Mölndal (SE); Peter Rünnberg, Mölndal (SE); Ponrus Winqvist, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 10/272,934

(22) Filed: Oct. 18, 2002

(65) Prior Publication Data

US 2003/0082970 A1    May 1, 2003

Related U.S. Application Data

(60) Provisional application No. 60/330,614, filed on Oct. 26, 2001.

(51) Int. Cl.
*A61F 13/15* (2006.01)
*A61F 13/20* (2006.01)

(52) U.S. Cl. .............. 604/385.03; 604/367; 604/385.01; 604/385.06

(58) Field of Classification Search .......... 604/358–402; 602/54, 48; 128/888–889; D24/188; 424/443, 424/447
See application file for complete search history.

(56) References Cited

U.S. PATENT DOCUMENTS

| 2,742,903 | A | * | 4/1956 | Lightner ...................... 604/387 |
| 3,042,549 | A | * | 7/1962 | Arnold et al. ................. 524/733 |
| 3,050,491 | A | * | 8/1962 | Nitzsche et al. .............. 524/588 |
| 4,661,099 | A | * | 4/1987 | von Bittera et al. .......... 604/290 |
| 4,684,557 | A | * | 8/1987 | Pennace et al. .............. 428/40.9 |
| 4,711,781 | A | * | 12/1987 | Nick et al. .................... 424/446 |
| 4,731,063 | A | * | 3/1988 | Newkirk ....................... 604/347 |
| 4,731,071 | A | * | 3/1988 | Pigneul .................... 604/385.23 |
| 4,753,645 | A | * | 6/1988 | Johnson ........................ 604/378 |
| 4,838,253 | A | * | 6/1989 | Brassington et al. .......... 602/48 |
| 4,959,059 | A | * | 9/1990 | Eilender et al. .............. 604/358 |
| 4,997,425 | A | * | 3/1991 | Shioya et al. ................. 604/304 |
| 5,019,064 | A | * | 5/1991 | Eilender ....................... 604/378 |

(Continued)

FOREIGN PATENT DOCUMENTS

DE    298 19 087 U1    4/2000

(Continued)

OTHER PUBLICATIONS

Office Action issued Jul. 22, 2008 in corresponding JP Appln No. 2003-537535.

*Primary Examiner* — Michele Kidwell

(74) *Attorney, Agent, or Firm* — Buchanan Ingersoll & Rooney PC

(57) ABSTRACT

An insert for use together with an absorbent article such as a diaper, an incontinence product, a sanitary towel, a panty liner or the like. The insert is substantially non-urine-absorbing and comprises a support sheet (2) which has a first surface (12) and a second surface (13), the first surface (12) being treated with a skincare agent (14), and the second surface (13) being substantially impermeable to the skincare agent. The insert further includes at least one spacing and liquid-receiving sheet (3) placed against the second surface (13) of the support sheet (2). The spacing and liquid-receiving sheet facilitates the intake of liquid through the topsheet when the insert is in use.

20 Claims, 3 Drawing Sheets

U.S. PATENT DOCUMENTS

| | | | | |
|---|---|---|---|---|
| 5,156,601 | A * | 10/1992 | Lorenz et al. | 604/307 |
| 5,348,547 | A | 9/1994 | Payne et al. | |
| 5,445,627 | A * | 8/1995 | Mizutani et al. | 604/385.28 |
| 5,540,922 | A | 7/1996 | Fabo | 424/402 |
| 5,556,393 | A * | 9/1996 | Ronnberg | 604/385.26 |
| 5,704,905 | A * | 1/1998 | Jensen et al. | 602/58 |
| 5,807,299 | A * | 9/1998 | McRoberts et al. | 602/67 |
| 5,843,018 | A * | 12/1998 | Shesol et al. | 602/79 |
| 5,919,476 | A | 7/1999 | Fischer et al. | 424/443 |
| 6,051,747 | A * | 4/2000 | Lindqvist et al. | 602/46 |
| 6,107,537 | A * | 8/2000 | Elder et al. | 604/364 |
| 6,120,783 | A * | 9/2000 | Roe et al. | 424/402 |
| 6,149,619 | A | 11/2000 | Gronholz | 604/20 |
| 6,183,770 | B1 * | 2/2001 | Muchin et al. | 424/448 |
| 6,200,195 | B1 * | 3/2001 | Furuno et al. | 450/81 |
| 6,211,426 | B1 * | 4/2001 | Abrams | 602/46 |
| 6,258,076 | B1 * | 7/2001 | Glaug et al. | 604/387 |
| 6,570,054 | B1 * | 5/2003 | Gatto et al. | 604/364 |
| 6,580,011 | B1 * | 6/2003 | Jennings-Spring | 602/41 |
| 6,627,787 | B1 * | 9/2003 | Roe et al. | 604/364 |
| 6,846,508 | B1 * | 1/2005 | Colas et al. | 427/2.31 |
| 6,963,019 | B2 * | 11/2005 | Binder et al. | 602/48 |
| 7,112,183 | B2 * | 9/2006 | Binder et al. | 602/75 |
| 7,264,615 | B2 * | 9/2007 | Sherrod et al. | 604/385.14 |
| 2003/0104039 | A1 | 6/2003 | Berthold et al. | |

FOREIGN PATENT DOCUMENTS

| | | |
|---|---|---|
| EP | 1 051 958 A1 | 11/2000 |
| EP | 1057872 A2 | 12/2000 |
| EP | 1 120 097 A2 | 8/2001 |
| EP | 1136050 A1 | 9/2001 |
| EP | 1 153 617 A1 | 11/2001 |
| WO | WO 94/15562 | 7/1994 |
| WO | 96/16682 | 6/1996 |
| WO | 99/22684 | 5/1999 |
| WO | WO 00/71177 A1 | 11/2000 |
| WO | WO 01/00154 | 1/2001 |
| WO | WO 01/22933 A1 | 4/2001 |
| WO | WO 01/43717 A1 | 6/2001 |
| WO | WO 01/070153 | 9/2001 |

* cited by examiner

INSERT FOR AN ABSORBENT ARTICLE WITH SKINCARE AGENT AND SPACING SHEET

CROSS-REFERENCE TO RELATED APPLICATIONS

The present application claims the benefit under 35 U.S.C. §119 of U.S. Provisional Application No. 60/330,614, filed in the United States on Oct. 26, 2001, the entire contents of which are hereby incorporated herein by reference.

BACKGROUND OF THE APPLICATION

1. Technical Field

An insert for use together with an absorbent article such as a diaper, an incontinence product, a panty liner or the like, which insert is substantially non-urine-absorbing, comprising a support sheet which has a first surface and a second surface, the first surface being treated with a skincare agent and the second surface being substantially impermeable to said skincare agent.

2. Background

A number of attempts have been made to produce skin-friendly absorbent articles such as diapers or incontinence products, sanitary towels, panty liners or the like. The surfaces which bear against the user's skin during use of the absorbent article are generally coated with, for example, creams, ointments, lotions or the like.

WO 96/16682 "Diaper having a lotioned topsheet" (Roe et al) describes a diaper with lotion on the liquid-permeable topsheet. According to said document, problems such as poor intake of liquid are solved by using hydrophilic lotion on the topsheet. The lotion is said not to interact with, for example, urine in the same way that a hydrophobic lotion would. The document also describes how cleaning the user's skin is made easier by the fact that the lotion is intended to be partially transferable to the user's skin in order, among other things, to prevent excrement from adhering to the skin. The diaper according to WO 96/16682 is also said to solve the problem of supplying therapeutic or protective components via small amounts of lotion which do not damage the liquid-handling capacity of the diaper and do not require special packaging.

However, the known diaper is associated with a number of problems. In any process in which lotion is added at high speed to a liquid-permeable material, it is in principle impossible not to partially block at least some of the pores on the liquid-permeable topsheet. Attempts at avoiding or at any rate minimizing this problem can be made by applying the lotion in lines or specific patterns on the liquid-permeable topsheet. However, the problem of blocked pores still remains in the coating pattern.

A further problem is that lotion can migrate downwards from the topsheet through the pores and thereby prevent the absorption body from taking up liquid. This problem is remedied by producing lotions and lotion stabilizers with specific melt temperatures which preferably will be completely or at least partially solid at room temperature and will begin to melt at temperatures preferably immediately below body temperature.

However, there are a number of problems in modifying lotion to obtain specific properties. For example, there is often poorer transfer of lotion to the skin, and sometimes this is even insufficient to give the desired skincare effect since the viscosity and the melt temperature have been changed. Despite modification of the lotion, the product is exposed before use, for example during transportation and storage, to circumstances, such as more extreme temperatures, which mean that the lotion can still migrate at least partially and thus impair the intake of liquid into the absorbent article by blocking the pores of the topsheet and thus indirectly also the absorption core. Migration of lotion to the absorption core can additionally cause a direct deterioration of the absorption capacity. The migration problems arise, for example, when the product is kept in a hot storage area. It may also be hot in the shop where the product is for sale, the product may be left lying in a luggage boot on a sunny summer's day, a pack of diapers may be left in the laundry room above a radiator until the time comes to use the pack, etc. Thus, there are obviously situations which cannot be safeguarded against merely by modifying the lotion so that it has a specific melt temperature.

WO 99/22684 "Web materials with two or more skin care compositions disposed thereon and articles made therefrom" (Roe et al) describes a web with at least two different kinds of skincare material. The web is attached at different points to a diaper, for example the topsheet, the liquid barriers or the like. Here once again, no particular attention is paid to the problem of blocking of the pores. In addition, there is not much scope for the user's requirements or desires regarding the position of the skincare agent. The document also points to a lack of understanding of an important problem in connection with skin care; the skin where it is desired to prevent or treat skin irritations, sores, rashes or bedsores must preferably be as undisturbed as possible. This means that the skin should be exposed to the least possible external influence. When using an absorbent article, for example an incontinence product or diaper, there is always a certain degree of chafing between the skin and the product. Chafing means that the skin becomes more susceptible and more sensitive to the negative effects of excrement and urine and to the environments which result in a product when it is exposed to this.

In those cases where ointment or lotion is applied directly to the skin before the absorbent article is secured on a user, some of the substance can still transfer to and penetrate into the topsheet and block the absorbent core with respect to urine for example. In addition, no continuous transfer of the skincare agent is obtained over the course of time. This means that when the applied skincare agent has been taken up completely by the skin, it is finished. Besides this, a person looking after a patient may find it unpleasant to apply a skincare agent directly to the skin, not only because the lotion or the like may be sticky to use, but also because the patient may have sores which are infected, and the patient may possibly have scabs which the carer does not want to deal with but has to. Similarly, the patient too may not want a carer to touch the sore or the sensitive skin directly with the hands.

DE 298 19 087 U1 "Pad oder Windeleinlage zur Trennung der zur Pflege oder Therapie auf Haut aufgetragenen Substanzen und der Windeleinlage" (Klaus) is a utility model which describes an insert which is intended to function as a dividing wall between the applied ointment, cream or paste and an absorbent article. The utility model also describes how the insert can be coated with an ointment, cream or paste which can also contain a biocatalyst and which, on the side remote from the skin, consists of web, foil or cotton intended to prevent the inner advancing of the substance on the outside diaper.

However, the known insert is only designed to keep the skincare agent on the skin and there is no discussion at all of the risk of deteriorated intake of liquid which the insert itself causes because of the blocking of the topsheet. In addition, the document does not mention nursing care problems such as bedsores caused by excessive loading of sensitive and perhaps damaged areas of the skin.

OBJECTS AND SUMMARY

It is therefore an object of the invention to propose a solution with greater flexibility as regards the viscosity and melt point of the skincare agent, in order to permit a good continuous transfer of the skincare agent. The invention is also aimed at solving the problem of the method of packaging in such a way that the lotion does not affect the absorbent article. The invention makes it possible to obtain sufficient transfer of lotion without the lotion negatively affecting the intake of liquid into the absorbent article or the absorption capacity of the absorbent article.

There is a need for a solution making it possible to use lotion in an absorbent article or the like both in order to prevent and also to alleviate rashes, skin irritations, pressure sores, bedsores and the like. There is also a need for a flexible insert which allows for more variations for skin care than do diapers with lotion in predetermined positions. There is also a need for an insert which minimizes chafing between the sensitive skin (damaged skin, or where skin damage is to be prevented) and the absorbent article. There is a need for an insert which not only protects but can also take up and distribute any loading across a greater surface area.

An embodiment of the present invention provides a substantially non-urine-absorbing insert which is of the type discussed in the introduction and which essentially eliminates the problems of the previously known inserts of this type. Such an insert comprises at least one further sheet which functions as a spacing and liquid-receiving sheet placed against the second surface of the support sheet. The arrangement of the spacing and liquid-receiving sheet facilitates the intake of liquid through the topsheet when the insert is in use.

"Substantially non-urine-absorbing" is to be understood as meaning that at least the so-called spacing and liquid-receiving sheet preferably will not retain substantially any urine after wetting has occurred. The spacing and liquid-receiving sheet should suitably transport liquid away, or at least should not to any great extent prevent liquid from reaching the absorption body. In purely practical terms, it is in principle difficult to avoid a few drops of liquid being held in a fibre structure because of the capillary forces which arise in different cavities and between the fibres. However, this is not desirable and is minimized according to the invention.

The insert should therefore be substantially nonabsorbent in order to help minimize the pores or holes in the liquid-permeable topsheet from being blocked and thus prevent liquid from penetrating into the absorption body and being absorbed by the core. Liquid should also be able to be transported through the topsheet upon repeated wetting.

The spacing sheet has a number of different functions. For example, as its name suggests, it is intended during use to separate the support sheet (which comprises at least one skincare agent and a barrier sheet) from the liquid-permeable topsheet. The separating property is important to help ensure that the topsheet (and thus indirectly also the absorption body) is not likely to be blocked by the barrier sheet. Liquid, for example urine or blood, should be able to pass beneath the barrier sheet in a free and relatively unimpeded manner. It is therefore also preferable for this reason that the spacing sheet is substantially non-urine-absorbing.

In order to ensure that the spacing sheet will not likely block the topsheet, it is preferable that it is liquid-permeable (i.e., that it does not prevent liquid from penetrating in through the topsheet) even when exposed to loading. The spacing sheet is therefore preferably made of a material which is rigid, for example, reticulated foam with an open pore structure. The spacing sheet should therefore be liquid-permeable in at least one direction, i.e., in the X, Y, or Z direction, and preferably in all directions. The spacing sheet can also be designed to make it easier in purely physical terms for liquid to penetrate through it, for example, by means of channels parallel to the liquid-permeable topsheet of the absorbent article, elevations or depressions in specific zones, or other three-dimensional structures. On that surface of the spacing sheet which during use is intended to bear against the absorbent article, further material can also be attached so that different three-dimensional structures are obtained.

When the user has sensitive skin and may possibly get or has a rash, irritation or bedsore, it is preferable that the surface of the sensitive skin is not exposed to chafing. Besides the fact that chafing can, in purely physical terms cause external damage to the skin, chafing also has the effect that the skin becomes more susceptible to other external influences such as excrement, urine and the extreme conditions which these cause. One embodiment of the invention solves this problem by means of the fact that the insert attaches directly to the skin with the aid of the skincare agent. Preferably no paste or adhesive is therefore used, since this too can cause irritation upon repeated use or in cases of allergies, for example. In one embodiment silicone gel is used as the securing means for the insert, as is described in more detail in GB-A-2192 142 and EP-A1-0,300,620. Silicone gels are soft and attach to the skin. There are also silicone gels which do not attach to sores. The extremely low tendency to attach to sores, compared to other securing means, is due to the low surface tension of the silicone gel and to a surface chemistry which gives rise to another type of adhesion forces to sores than is obtained with an adhesive, for example. This means that the silicone gel is able to stick to tender, ulcered areas of the skin where adhesive would not be suitable as securing means. In this respect, silicone gel has a skincare effect and can be said to be a skincare agent per se. The silicone gel can comprise further skincare agents or can be combined with a separate skincare agent. The silicone gel can be applied in strips or patterns on the surfaces which are intended to be attached to the skin. In the last-mentioned design, the silicone gel is expediently placed across surfaces which are not covered with skincare agent, for example at the edges of the insert.

After application, the insert is held in place with the aid of the outside absorbent article, for example a diaper, incontinence product, panty liner or the like, but without the insert being secured to the absorbent article. That surface of the insert which during use is intended to bear against the absorbent article will preferably have as low a friction as possible against the absorbent article in order to minimize shearing forces which occur between the insert and the absorbent article and which can give rise to chafing of the user's skin. The insert is thus free from the absorbent article in the sense that the insert is not secured to the absorent article during use but is only pressed against the skin by the absorbent article. In addition, the insert is held in place by being secured to the skin with the aid of the skincare agent. This means that the surface exposed to shearing forces is shifted from the skin to the surface of the insert which during use bears against the absorbent article. Thus, the risk of chafing of the user's skin is reduced by means of the invention.

In order also to relieve sensitive areas of skin so that, for example, localised pressure on the skin is distributed over a greater surface area, it is expedient if the spacing sheet is to some extent elastically compressible. This means that a desired property of the spacing sheet is that it can return to its original shape after loading. It should also be able to damp shocks or be conformable so that it retains its shape at least for a while after the load has ceased. It may also be desirable for the spacing sheet to be sufficiently rigid or pressure-resistant so that it is not compressed completely when loaded with a substantial weight. The aim of this is, of course, as has already been mentioned, so that the insert will be able to take up loads in specific areas of the skin which may be or may conceivably become exposed to discomforting and damaging loads. The shearing forces which can form between the absorbent article and the user can also be taken up or at least counteracted by a flexible material in the insert.

According to one embodiment, the spacing sheet comprises a material which recovers its shape after it has been exposed to loading. The degree of recovery can be measured by a simple method:

1. The height Ho (thickness) of the material is measured.
2. The material is then exposed to a load of 200 kPa (>>49.8 g/cm$^2$) for a defined period of time.
3. Thereafter, the height $H_1$ is measured immediately after the loading has ceased (directly means within about one minute).
4. The height $H_2$ is measured about 1 hour after the loading has ceased.
5. The height $H_3$ is measured about 4 hours after the loading has ceased.

The degree of recovery at different points in time can thus be calculated by $(H_1/H_0) \cdot 100$, $(H_2/H_0) \cdot 100$ or $(H_3/H_0) \cdot 100$. It may be difficult to obtain a reproducible measured value of the height immediately after the loading has ceased (i.e., within one minute) for a material which recovers quickly. It is therefore preferable that the height is measured after the same length of time for each sample. If the first sample is measured after about 15 seconds, it is preferable to ensure that the following sample is also measured after about 15 seconds, in order to obtain a value which is as reproducible as possible.

A Mitutoyo® ID-U1025 can be used, for example, to obtain a precise value of the height. An important point, however, is that the height is measured in the same manner for all heights, so that a reproducible value is obtained.

According to one embodiment, the spacing sheet comprises a material which has a degree of recovery of about 70-100%, preferably 50-100%, and most preferably 20-100% immediately after the loading has ceased. Moreover, the degree of recovery is preferably about 70-100%, preferably 50-100%, and most preferably 20-100% about 1 hour after the loading has ceased, and preferably about 70-100%, preferably 50-100%, and most preferably 20-100% about 4 hours after the loading has ceased.

According to one embodiment, the spacing sheet is made of a material which has a free volume (or void volume) of 1-95% of the total volume of the insert. By varying the free volume of the spacing sheet, different properties of the spacing sheet can be obtained. A spacing sheet with a free volume of over 40% of the total volume of the insert is highly porous with cavities in the material. A sufficiently porous material functions as a distribution sheet which makes it easier, for example, for urine to be absorbed by the core since the topsheet is not blocked. Another advantage of a highly porous spacing and liquid-receiving sheet is that a large quantity of liquid can be received in a short time.

In one embodiment, the support sheet comprises a separate skincare layer and a barrier layer, the barrier layer being placed between the skincare layer and the spacing sheet.

In another embodiment, entirely penetrating holes are formed in the support sheet. This can be done to make it easier for the skin to breathe. The support sheet in this case has a multiplicity of holes or pores and has an effective open area of at least 10%, the open area of the holes or pores preferably being at least 0.1 mm$^2$ per hole or pore. (Effective open area is to be understood as the sum of the open area of the individual holes in relation to the area of the first surface of the support sheet. Open area is to be understood as that area of the hole or pore which lies in the same plane as the first surface of the support sheet). Depending on how important it is to allow the skin access to air, the area of the holes and thus the effective open area can be varied.

It should be noted that the absorption capacity of the skin increases for most materials if the skin is occluded, i.e., covered (H. Schaefer, T. E. Redelmeier, "Skin barrier—Principles of percutaneous absorption", page 167, 1996). Therefore, for certain applications, it may be desirable for the support sheet not to have any completely continuous holes.

For the substantially non-urine-absorbing insert to be held in place with the aid of the skincare agent, it is preferable that the skincare agent attaches to the skin. The skincare agent should therefore be sticky, that is to say sticky enough to ensure that the insert remains on the skin and does not fall off directly after application. The use of adhesive or the like as securing means is preferably avoided since adhesive often gives rise to skin irritation or allergic reactions upon repeated use. It is therefore preferable for the skincare agent itself to be able to function as the substance for securing the insert to the skin.

The viscosity of the skincare agent is in some cases a measure of how sticky the skincare agent can be. If the viscosity is too high, so that the skincare agent is completely solid in consistency, it may not function as a means of securing the insert. Nor is it possible to obtain any significant transfer of the skincare agent to the skin, at least not before it has completely or partially melted as a result of the body heat. One of the advantages of the invention, however, is that it permits a greater viscosity range for the skincare agent than is possible when, for example, lotion or the like is applied to the topsheet of a diaper, since the skincare agent can be coated on and/or impregnated in the support sheet.

The invention is also distinguished by the fact that it is possible to arrange a large quantity of skincare agent on the support sheet. A large quantity of skincare agent ensures a good transfer and a continuous transfer. The support sheet preferably comprises at least 0.1 mg of skincare agent per cm$^3$ of support sheet.

BRIEF DESCRIPTION OF THE FIGURES

The embodiments of the invention will be described in more detail below with reference to the figures which are shown in the attached drawings, where.

DETAILED DESCRIPTION OF PREFERRED EMBODIMENTS

Figure 1:
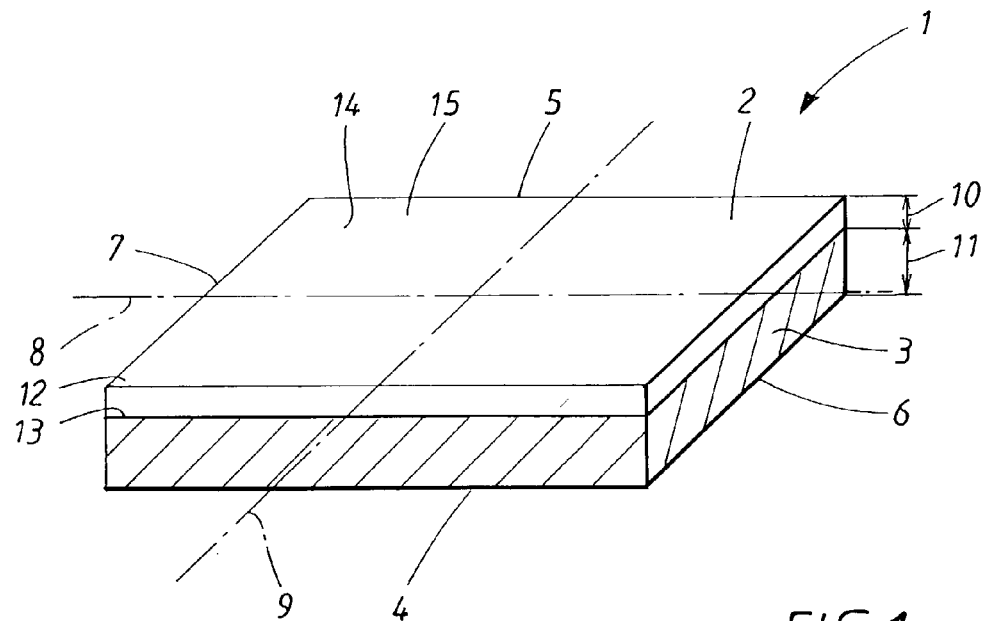
FIG. 1 shows an insert comprising a support sheet and a spacing sheet.

The insert 1 shown in FIG. 1 comprises a support sheet 2 and a spacing sheet 3 which together have a generally elongate form. The two sheets 2, 3 each have two longitudinal sides 4, 5 and two transverse sides 6, 7, a longitudinal center line 8 and a transverse center line 9. The support sheet 2 moreover has a first thickness 10 and the spacing sheet has a second thickness 11.

The support sheet 2 according to FIG. 1 has a first surface and a second surface 12, 13, the first surface 12 being treated with a skincare agent 14. The skincare agent 14 can be applied to the top of the first surface 12 and forms a top layer 15, can be impregnated in the first surface 12 or applied so that the skincare agent 14 completely or partially migrates into the first surface 12 and thus also partially into the support sheet 2. The first surface 12 can also be called the skincare surface 12.

The second surface 13 of the support sheet 2 is substantially impermeable to the skincare agent 14 and can be obtained by a modification of the material, such as heat treatment, pore gradient, change of surface energy or the like, and can also be called a barrier layer.

The support sheet 2 can also consist of a laminate in which the skincare surface 12 consists of at least one individual sheet. The second surface 13 of the support sheet can also consist of at least one individual sheet. The support sheet 2 can also consist of at least two connected laminates.

The support sheet 2 and the spacing sheet 3 can consist of a number of different materials, for example the support sheet 2 and the spacing sheet 3 can consist of a nonwoven, a woven material, film, foam, elastic web or combinations of these. Preferred sheet materials can include polyolefins, for example polyethylene including linear low-density polyethylene (LLDPE), low-density polyethylene (LDPE), ultra-low-density polyetheylene (ULDPE), high-density polyethylene (HDPE), or polypropylene and/or mixtures of said materials. Further examples of suitable polymeric materials which could be used are polyesters, polyurethanes, compostable or biodegradable polymers, heat-sensitive polymers, thermoplastic elastomers, metalycene catalyst-based polymers (for example Insite™ which is commercially available from DOW Chemicals and Exxact™ which is commercially available from Exxon), and breathable polymers or vapour-permeable (breathable) materials. The web can also consist of or comprise a synthetic web, perforated nonwoven or film, macroscopically expanded three-dimensional films, foam material, filled composiitons or laminates and/or combinations of these. Nonwoven material can be produced by being what is called spun-bonded, liquid perforated, liquid entangled, carded, air-bonded, calendered or combinations of these. However, according to a preferred embodiment of the invention, the support sheet 2 and the spacing sheet 3 are substantially non-urine-absorbing (the insert may in some circumstances retain very small quantities of liquid) and the material of at least the spacing and liquid-receiving sheet should therefore consist of a substantially hydrophobic material, for example, synthetic fibers such as polyolefin fibres which have not been treated with a wetting agent.

As has already been mentioned, the support sheet 2 and the spacing sheet 3 can also be laminates of previously mentioned materials combined in a number of ways known in the art. In the same way or in a similar way, the support sheet 2 and the spacing sheet 3 can also be joined together, for example, by thermal binding, adhesion, for example with spray adhesive, hotmelt, latex-based adhesive or the like, ultrasound welding, or extruder lamination, which involves a polymer film being laid directly on a substrate while the film is still in the partially melted state and thereby adheres to the substrate. Said laminates can consist of one or more sheets of elastic layers, preferably compression-elastic and/or nonelastic layers.

It is also conceivable within the scope of the invention that the support sheet and the spacing sheet consist of a single sheet and that the skincare agent is applied to the first surface of the sheet and that the barrier part consists of a section positioned between said first surface and the second surface of the sheet.

The support sheet 2 is impregnated and/or coated with a skincare agent 14 such as a lotion or the like which, during use, secures the insert 1 to the user's skin in such a way that the skincare agent 14 is afterwards partially transferred to the user.

Figure 2:
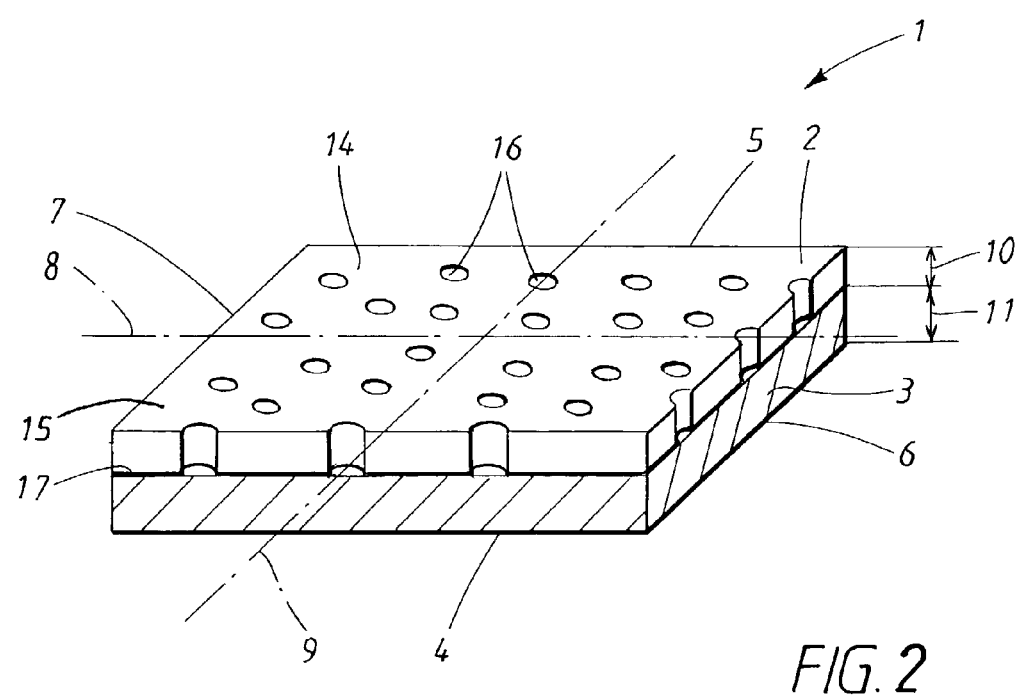
FIG. 2 shows an insert with a specific design of the support sheet.

A further embodiment of the insert 1 is shown in FIG. 2, comprising a support sheet 2 and a spacing sheet 3 which together have a generally elongate form. The two sheets 2, 3 also each have two longitudinal sides 4, 5 and two transverse sides 6, 7, a longitudinal center line 8 and a transverse center line 9. The support sheet additionally has a first thickness 10 and the spacing sheet has a second thickness 11.

The support sheet 2 in FIG. 2 has a number of through-holes 16 which extend through the entire thickness 10 of the support sheet 2. The support sheet 2 comprises a skincare layer 15 and a barrier layer 17 which is substantially impermeable to the skincare agent 14. It is possible, within the scope of the invention, that the holes 16 do not go through the barrier layer 17, which in that case preferably consists of a substantially vapour-permeable material. It is also possible, within the scope of the invention, that the holes 16 extend through the whole insert, i.e., that the holes 16 go through both the thickness 10 of the support sheet 2 and the thickness 11 of the spacing sheet 3.

Figure 3:
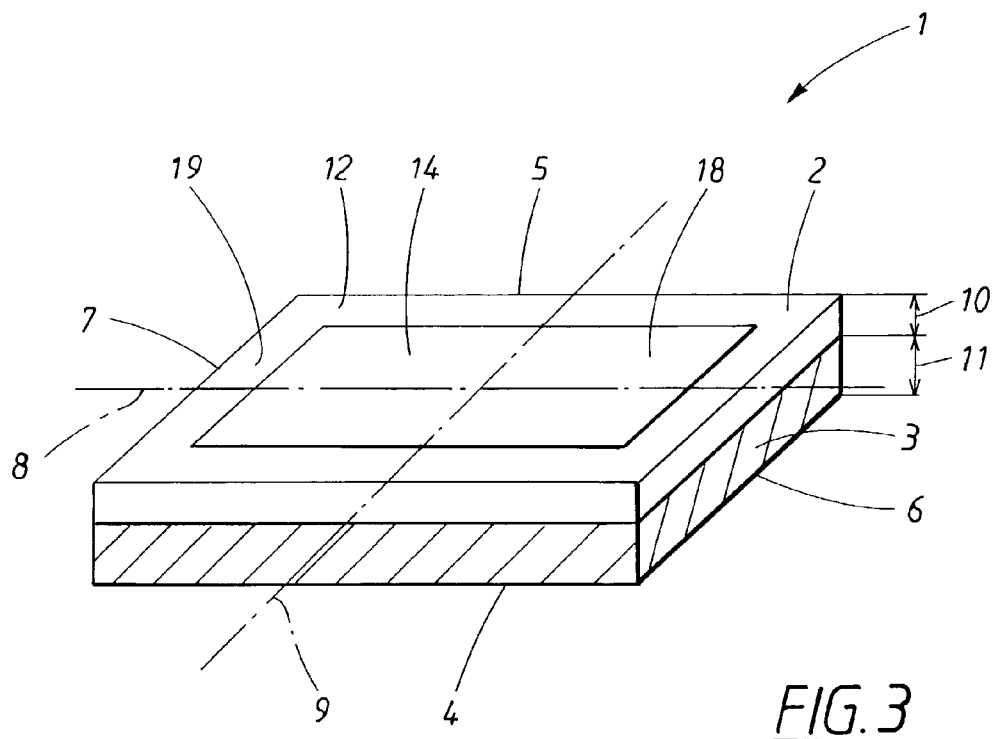
FIG. 3 shows an insert with a specific design of a coating of skincare agent.

A further embodiment of the insert 1 is shown in FIG. 3 and comprises a support sheet 2 and a spacing sheet 3 which together have a generally elongate form. The two sheets 2, 3 each have two longitudinal sides 4, 5 and two transverse sides 6, 7, a longitudinal center line 8 and a transverse center line 9. The support sheet additionally has a first thickness 10 and the spacing sheet has a second thickness 11.

FIG. 3 shows the skincare agent 14 arranged in the form of a rectangle 18 on the first surface 12 of the support sheet 2. The rectangle 18 is coated on the first surface 12 of the support sheet such that the area of the applied skincare agent 14 is smaller than the total area of the first surface 12 of the support sheet and such that there is a remaining area 19 around the rectangle 18 not coated with skincare agent 14. However, it is alternatively possible, within the scope of the invention, that the area of the skincare agent 14 is substantially the same size as the area of the first surface 12 of the support sheet 2.

It is also possible, within the scope of the invention, that the skincare agent 14 can be applied in a number of different shapes, i.e., it does not need to be a rectangle. For example, the skincare agent 14 can be applied in a circular shape or rhomboid shape, the skincare agent 14 could have three, four, five or more edges, and irregular shape, but also a number of other shapes. The skincare agent 14 can also be in different patterns such as squares, stripes, dots, circles, simple pictures of objects, logos, animals, plants or the like.

The spacing sheet 3 can have a number of different designs. The thickness 11 of the spacing sheet 3 can, for example, be smaller than, larger than or the same size as the thickness 10 of the support sheet 2. The thickness 11 of the spacing sheet 3 can also be different at different locations of the spacing sheet 3, i.e., there can be a certain three-dimensional structure. As it is desirable that the material of the spacing sheet 3 is permeable to air and liquid, especially in association with the liquid-permeable topsheet of an absorbent article, three-dimensional structures can be formed which make this easier, for example, channels or the like which run parallel to the liquid-permeable topsheet of the absorbent article.

Other properties which may conceivably be desirable for the spacing sheet 3 are that it can recover its original shape after loading, and that it will be able to have a shock-damping function or be conformable so that the spacing sheet 3 retains its shape at least for a while after the loading has ceased. It can also be desirable that the spacing sheet 3 is sufficiently rigid and pressure-resistant to ensure that it is not completely compressed when loaded with a considerable weight. This is of course, as has already been mentioned, to ensure that the insert will, during use, relieve the load on specific areas of the skin which may be or may conceivably become exposed to discomforting and/or damaging load. It is also important that the spacing and liquid-receiving sheet of the insert can receive liquid under a certain loading.

Figure 4:
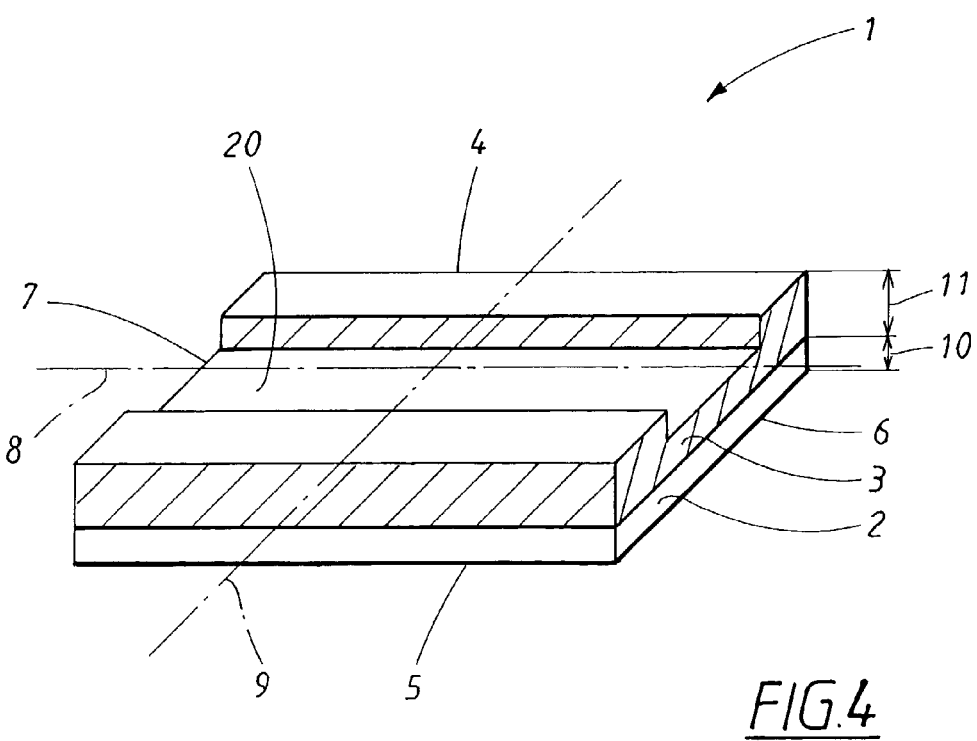
FIG. 4 shows an insert with a specific design of the spacing sheet.

A further embodiment of the insert 1 is shown in FIG. 4, comprising a support sheet 2 and a spacing sheet 3 which together have a generally elongate form. The two sheets 2, 3 each have two longitudinal sides 4, 5 and two transverse sides 6, 7, a longitudinal center line 8 and a transverse center line 9, and the support sheet has a first thickness 10 and the spacing sheet has a second thickness 11.

The spacing sheet 3 has a channel 20 which extends substantially in the direction of the longitudinal center line 8 of the insert. The channel 20 can be produced by compression of the spacing sheet 3, hollowing-out material, or by attaching further material along the longitudinal sides 4, 5 of the spacing sheet 3. It is also possible, within the scope of the invention, to arrange a number of channels extending either in the direction of the longitudinal center line 8 of the insert 1 or the transverse center line 9 of the insert 1. Other types of patterns are also conceivable, for example circular, square or the like. An important point in this embodiment is that the configuration of the spacing sheet 3 is such that intake of liquid through or past the spacing sheet 3 is facilitated.

Figure 5:
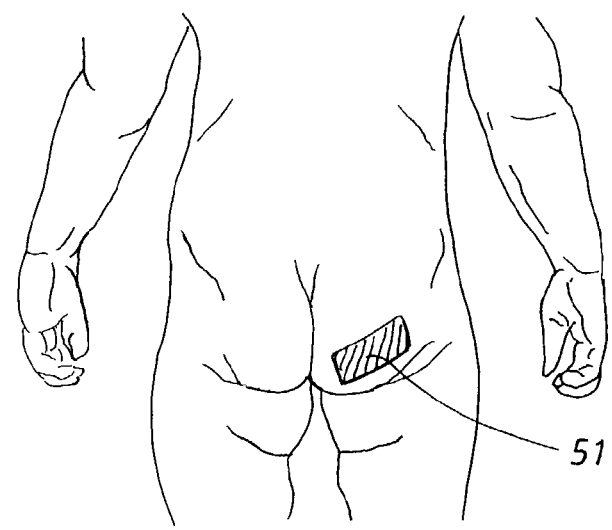
FIG. 5 shows a person, seen from behind, with an insert secured to the skin before the absorbent article is applied.
Figure 6:
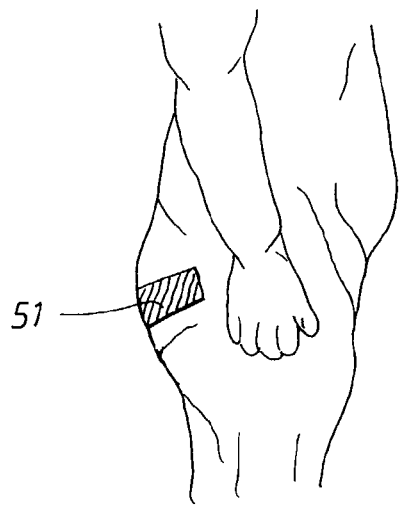
FIG. 6 shows a person, seen from the side, with an insert secured to the skin before the absorbent article is applied.

FIG. 5 shows a user, seen from behind, with an insert 51 secured to the skin. FIG. 6 shows the same user seen from one side. The insert is secured to one of the user's buttocks, although the insert can in principle be secured at any position on the user which is to be treated or where treatment is to be avoided. After the insert has been secured, an absorbent article 53 is applied to the user in a customary manner.

The insert can have a rectangular shape as in FIGS. 5 and 6, but it is also possible within the scope of the invention for the insert to have another shape, such as a shape with three or more edges, oval, circular, rhomboid, irregular or similar shape. The insert can also have the shape of a vehicle, house, plant, figure, or any other shape which it may be imagined could be desirable. The size of the insert can also be varied, for example the skincare side of the insert can have an area of about 2-500 $cm^2$, preferably 40-350 $cm^2$, most preferably 80-200 $cm^2$. The size of the insert can if necessary be adapted depending on the type of treatment desired, the person who is to use the insert, and the type and size of the absorbent article. There may even be advantages to be gained in terms of production engineering by designing the insert in a specific way, for example, in order to minimize wastage during manufacture of the insert.

The shape of the insert can be varied depending on where it is intended to be placed on the user. As it is within the scope of the invention for the insert to be placed anywhere on the body, and specifically to the inside of an absorbent article, the insert can be made available in different sizes and shapes. A general rule of thumb should be that large inserts are used for large treatment surfaces and small inserts for small treatment surfaces, or alternatively a number of small inserts for a large treatment surface. Treatment surface is to be understood as meaning the surface of the user's skin which is intended to be treated with the skincare agent.

Figure 7:
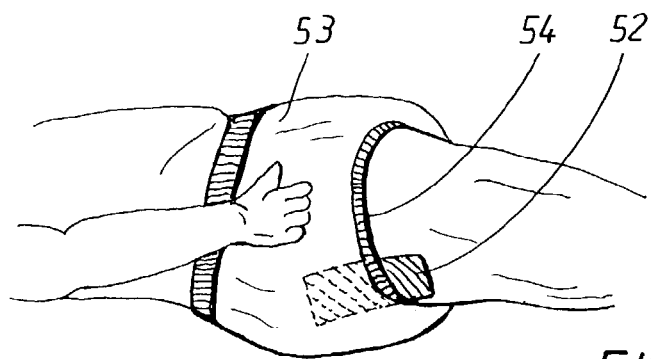
FIG. 7 shows a person lying supine with an insert secured to the skin and an absorbent article around the waist and hip region.

FIG. 7 shows a person with a bedsore (pressure sore) lying supine. An insert 52 is applied on one leg and buttock. The insert 52 extends slightly outside the absorbent article 53 and thus affords, in addition to a good skincare effect, a support and relief from the leakage barriers 54 of the absorbent article 53. Leakage barriers are often found in the leg area of absorbent articles such as diapers or incontinence products. Examples of absorbent articles with leakage barriers (also called liquid barriers) are described in, for example, WO-A1-9207533, U.S. Pat. Nos. 4,695,278, 5,064,489, SE-T3-0264238 and GB-A-2188532. Examples of how an incontinence product can appear are described inter alia in WO 99/21522 A1. In the same way, the insert can also afford support and relief at the waist or at other locations where the absorbent article may conceivably be to tight or give rise to uncomfortable chafing. The insert extends in across the liquid-permeable topsheet (not shown in the figure) of the absorbent article 53.

The above should not be regarded as limiting the invention to use together with only those absorbent articles described in said references, and instead all forms of absorbent articles known to the skilled person in the field of diapers, incontinence products, sanitary towels, panty liners, or the like are to be regarded as being included.

Diaper Dermatitis

Several factors in combination lead to the development of diaper dermatitis. Wet skin results in that chafing and pressure more easily wear down the skin. A high moisture content also means that skin penetration by irritant substances can increase, and that bacteria and fungi can thrive. Occlusion of skin and breakdown of urea in the urine to ammonia results in an increase in the pH. The higher pH value leads to that enzymes (lipases and proteases) coming from the intestine, and from microorganisms in the excrement, can break down the skin to a greater extent. A vicious circle can easily develop in which various factors faciliate and intensify each other.

Dermatitis is best prevented by creating conditions which counteract those factors which create and maintain the process of diaper dermatitis. It should therefore be endeavoured to keep the skin as dry as possible, to air the skin often and to change wet diapers. Mechanical shearing forces should be minimized by choosing materials which are as smooth and soft as possible, and wear between diaper and skin should be minimized. By supplying the skin with a softening and protective lotion or cream, it is further possible to strengthen the barrier against penetration of irritant substances and enzymes. In more serious cases of dermatitis, microorganisms may have infected the damaged skin, and treatment with more active medicines is required. Ointments with cortisone and various fungicidal and bactericidal agents are then used.

Examples of Skincare Agents to be Used in an Insert

Skincare agents can be used to prevent, alleviate or heal dermatitis. A skincare agent can consist, in its physical form, of a solution, suspension, cream, lotion, ointment, paste, gel, foam, aerosol or capsule, or it can be present in solid phase as particles, flakes, fibres, films, foams, waddings, sticks, etc. In the following description, a cream, lotion or ointment is preferably used, but others of the above-described forms are of course also conceivable.

Skincare agents can include lipids (fats, oils, waxes), solvents (including water), water-soluble substances, surface-active agents (emulsifiers, surfactants), viscosity-regulating substances, pH-regulating substances, preserving agents, complexing agents (e.g. chelates), delivery systems (e.g. liposomes, microcapsules, etc), pigments, pefumes, and active substances (also pharmaceutical agents). The lipids are usually emulsified in water, known as o/w emulsion, or water is emulsified in the lipid phase, known as w/o emulsion.

Skincare agents can include lipids such as:

Paraffins (alkanes) with 12-35 carbon, for example, paraffin oil (mineral oil) or petrolatum (vaseline).

Triglycerides, refined and/or hydrogenated, animal or vegetable with preferably carbon chain lengths of under C-18 (e.g. milk fat, coconut oil *Cocous nocifera*, palm-kernel oil *Elaeis guineeis*), animal or vegetable with unsaturated C-18 fatty acids (e.g. Japan wax *Rhus succesdanes*, tallow fat, soybean oil *Glycerin soya*, peanut oil *Arachais hypogaea*, maize oil *Zea mays*, sunflower oil *Helanthus annus*, grapeseed oil *Vitis vinifera*, safflower oil *Carthamus tinctorius*, sweet almond oil *Prunnus amygdalus dulcis*, hazelnut oil *Corylus americana*, walnut oil *Juglans regia*, olive oil *Olea europasa*, avocado oil *Persea gratissima*, sesame oil *Sesamum indicum*, tall oil, Tallol, cottonseed oil Gopssyipium, palm oil *Elaesis guineensis*, rice oil *Oryza sativa*, rape oil Canola, apricot-kernel oil *Prunus armeniaca*, cocoa butter *Theobroma cao*, shea butter *Butyrospermum parkii*, wheatseed oil *Triticum vulgare, Bassia latifola*), animal or vegetable with carbon chains over C-18 (e.g. beeswax *Cera alba*, shellac wax *Shellac cera*, meadowfoam seed oil *Limnanthes alba*, rapeseed oil *Brassica capmestris*, cucumberseed oil *Borago officinalis*, linseed oil *Linum usitatissimum*, ricin oil *Ricinus communis*, veronia oil *Veronia galamensis*, jojoba oil *Buxus chinensis*, candlewax *Euphorbia cera*, ongokea oil *Ongokea gore*).

Fatty alcohols with straight or branched carbon chain lengths of 12-32 carbons. For example, cetyl alcohol or stearyl alcohol.

Fatty acid esters with 12-32 carbons. For example, methyl palmitate, methyl stearate, isopropyl myristate, isopropyl laurate, isopropyl palmitate, isopropyl stearate, octyl palmitate, octyl stearate or octyl laurate.

Polyalcohols. For example, sugar alcohols or polyglycerols.

Complex lipids. For example, phospholipids or sphingolipids (ceramides).

Waxes. Of animal origin, for example beeswax or lanolin. Of vegetable origin, for example carnauba or candelilla. Of mineral origin, for example ozocerite or ceresin.

Polysiloxanes. Straight, branched or cyclic. For example, polydimethyl-siloxane (dimethicone) or polydiethylsiloxane.

Skincare agents can include emulsions such as:

Emulsions of one or more fats with hydrophilic substances such as water, glycerol, polyethylene glycol (PEG), propylene glycol, butylene glycol, sorbitol, silicone glycols or the like or mixtures thereof.

Skincare agents can include substances which adsorb irritating components in urine or excrement. For example, clay mineral (bentonite, kaolin, montmorillonite, etc), silicon oxide compounds (quartz, zeolites, water glass, etc) or activated charcoal. The substances can advantageously have been activated to be more adsorbent by means of various treatments, for example with quaternary ammonium compounds.

Skincare agents can include enzyme inhibitors. For example, metal salts of iron or zinc, trace amounts of heavy metal ions such as copper or silver, ethylene diamine tetraacetic acid (EDTA), soybean trypsin inhibitor, lima bean protease inhibitor, maize protease inhibitor, stearylglycyrrhetinate, glycerol triacetate, betaine compounds, sulphobetaine compounds, cholestyramine, p-guanidinobenzoates.

Skincare agents can include pH-regulating additives. For example, organic or inorganic acids such as adipic acid, ascorbic acid, benzoic acid, citric acid, malic acid, tartaric acid, lactic acid, phosphoric acid or hydrochloric acid. Or buffers made for example from said acids with corresponding salts. Can also include polymeric acids, for example polyphosphoric acid or polyacrylic acid.

Skincare agents can also include additions of probiotic microorganisms, characterized by being antagonistic towards undesired microorganisms, e.g., urinary tract pathogens or skin infection pathogens. Examples of probiotic microorganisms which can be used are individual strains or mixtures of several strains of lactic acid bacteria taken from the species *Lactobacillus acidophilus, Lactobacillus curvatus, Lactobacillus plantarum* or *Lactococis lactis*.

Skincare agents can also include more or less active substances such as:

Anti-inflammatory agents, e.g. acetylsalicylic acid, allantoin, azulen, alpha-bisabolol (chamomile), flavonoids, glycyrrhizinic acid, ichthammol (Inotyol®), tannins. Astringents (vasoconstrictors), for example TiO, ZnO (and other Zn compounds), aluminium acetate solution, aluminium tartrate solution (and other Al compounds), ethanol or ethanol-based solutions.

Aloe vera (*Aloe barbadensis*), alpha-hydroxy acids (citric acid, tartaric acid, lactic acid, malic acid, etc.), algae extract, ascorbic acid (vitamin C), vitamin A compounds (retinol, retinal, tretinoin and isotretinoin), avocado sterols, betaine (trimethylglycine), ceramides, grapeseed extract, essential fatty acids, flavonoids, phytosphingosine, phytosterols, hyaluronic acid, yeast extract, chitosan, milk protein (*Lactis proteinum*), pantenol (provitamin B5), polysaccharides, rosemary extract, tocopherol (vitamin E), ubiquinone (coenzyme Q10), urea.

Antimicrobial agents, for example amorolfin, antibiotics, bacitracin, benzalkonium chloride, benzetonium chloride, cetrimide, fusidic acid, gentian violet (methylrosaniline chloride), hexachlorophene, hexylresorcinol, imidazole derivatives (for example biphonazole, econazole, ketoconazole, chlotrimazole, miconazole), chlorhexidine, nystatin, povidone-iodine, terbinafin, triclosan, hydrogen peroxide.

Antiviral agents, for example acyclovir, imiquimod, podophyllotoxin, podophilox, cidofovir, penciclovir, vidarabin, idoxuridine, trifluridine, tromantadine, lamivudine.

Skincare agents can also include glucocorticoids, preferably of low potency, for example hydrocortisone, or antipruritic, for example antihistamines or local anaesthetics (e.g. lidocaine).

Skincare agents can also consist of ready-made mixtures of skin ointments, creams and lotions. For example, Necesse® Lotion (ingredients: aqua, propylene glycol, liquid paraffin, octyl octanoate, urea, PEG-8 distearate, steareth-2, steareth-21, betaine, lactic acid, tocopheryl acetate, dimethicone, tromethamine, methylparaben, propylparaben, perfume), Necesse® Skin Cream (ingredients: aqua, liquid paraffin, octyl stearate, sodium chloride, urea, glyceryl stearate, stearic acid, cetearyl alcohol, PEG-30 stearate, tocopheryl acetate, tromethamine, dimethicone, methylparaben, sorbic acid, propylparaben, perfume), Necesse® Barrier Cream (ingredients: petrolatum, glycerol, Arachis hypogaea, triethyl citrate, tocopheryl acetate) or Necesse® Zinc Ointment (ingredients: petrolatum, *Arachis hypogaea*, zinc oxide, retinyl palmitate, tocopherol). Necesse® products are sold commercially by SCA Hygiene Products, Gothenburg, Sweden.

Other examples of some different skincare agents and/or substances that can be used with the invention are described partially inter alia in the following documents: WO 96/16682

"Diaper having a lotioned topsheet" (Roe et al.), WO 96/16681 "Diaper having a lotioned topsheet containing a polysiloxane emmollient" (Roe, Mackey), WO 97/05909 "Diaper having a lotioned topsheet comprising a liquid polyester emollient and an immobilizing agent" (Roe), WO 99/45973 "Disposable absorbent article having a skin care composition containing an enzyme inhibitor" (Roe et al.), WO 99/45974 "Protease inhibitors in absorbent products" (Rourke et al.), WO 99/45976 "Proton donating actives in absorbent articles" (McOsker et al.), DE 33 09 530 C1 "Hygienische Absorptionsvorlage" (Leitner et al.), DE 41 36 540 A1 "Einwegwindeln" (Grunecker et al.), U.S. Pat. No. 3,489,148 "Topsheet for disposable diapers" (Duncan et al.), WO 00/64502 "Absorbent article having a lotionized bodyside liner" (Krzysik et al.), WO 00/64501 "Skin-friendly absorbent articles and compositions" (Krzysik et al.), WO 00/64500 "Absorbent article having a hydrophilic lotionized bodyside liner" (Krzysik et al.), WO 00/64503 "Skin-friendly absorbent articles and compositions" (Krzysik et al.), WO 99/22684 "Web materials with two or more skin care compositions disposed thereon and articles made therefrom" (Roe et al.).

It should be noted that the invention is not limited to the skincare agents just mentioned and that instead these are just examples of what could be used. The invention will preferably not make use of completely solid compositions of skincare agents since the aim is that the skincare agent will to some extent secure the insert to the skin.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An insert comprising:
   a skin care agent and substance for securing the insert to skin of a user;
   a support sheet; and
   a spacing and liquid-receiving sheet,
   wherein the support sheet has a first and second surface,
   wherein the spacing and liquid-receiving sheet has a first and second surface,
   wherein the skincare agent is located on the first surface of the support sheet such that the skin care agent forms a layer on the support sheet or impregnates the support sheet and completely or partially migrates into the support sheet,
   wherein the second surface of the support sheet is substantially impermeable to the skincare agent,
   wherein the support sheet, without the skincare agent and substance for securing the insert to skin of a user, is non-adhesive,
   wherein the first surface of the spacing and liquid-receiving sheet is placed against the second surface of the support sheet,
   wherein the second surface of the spacing and liquid-receiving sheet is an exterior surface of the insert,
   wherein the spacing and liquid-receiving sheet is permeable to liquid in all directions, and
   wherein the insert is substantially non-urine absorbing.

2. The insert according to claim 1, wherein the spacing and liquid-receiving sheet comprises a material which has a degree of recovery, after loading, of about 70-100% immediately after the loading has ceased.

3. The insert according to claim 1, wherein the spacing and liquid-receiving sheet comprises a material which has a degree of recovery, after loading, of about 50-100% immediately after the loading has ceased.

4. The insert according to claim 1, wherein the spacing and liquid-receiving sheet comprises a material which has a degree of recovery, after loading, of about 20-100% immediately after the loading has ceased.

5. The insert according to claim 1, wherein the spacing and liquid-receiving sheet has a free volume which is 1- 95% of the total volume of the insert.

6. The insert according to claim 1, wherein, the support sheet has a multiplicity of holes or pores and has an effective open area of at least 10%, the open area of each of the holes or pores being at least 0.1 mm$^2$.

7. The insert according to claim 1, wherein the support sheet comprises a vapour-permeable material.

8. The insert according to claim 1, wherein the skincare agent is suitable for use for preventing, relieving or healing dermatitis.

9. The insert according to claim 1, wherein the skincare agent comprises at least one of pH-regulating substances, antimicrobial substances, glucocorticoids, antiviral agents, probiotic microorganisms, enzyme inhibitors, and anti-inflammatory substances.

10. The insert according to claim 1, wherein the support sheet comprises at least 0.1 mg skincare agent per cm$^3$ of the support sheet.

11. The insert according to claim 10, wherein a side of the spacing and liquid-receiving sheet facing away from the support sheet has at least one longitudinal channel which extends substantially in a direction of the longitudinal center line of the insert.

12. The insert according to claim 1, wherein the skincare agent can function as the substance for securing the insert to the skin.

13. The insert according to claim 1, wherein the substance comprises a silicone gel which secures the insert to the skin.

14. The insert according to claim 1, wherein the skincare agent comprises a silicone gel.

15. The insert according to claim 1, wherein the spacing and liquid-receiving sheet is substantially non-urine-absorbing.

16. The insert according to claim 1, wherein the spacing and liquid-receiving sheet is substantially non-urine-absorbing and wherein the support sheet is substantially non-urine-absorbing.

17. The insert according to claim 1, wherein the spacing and liquid-receiving sheet is elastic in at least one direction.

18. An insert comprising:
   a skin care agent and substance for securing the insert to skin of a user;
   a support sheet; and
   a spacing and liquid-receiving sheet,
   wherein the support sheet has a first and second surface,
   wherein the spacing and liquid-receiving sheet has a first and second surface,
   wherein the skincare agent is located on the first surface of the support sheet such that the skin care agent forms a layer on the support sheet or impregnates the support sheet and completely or partially migrates into the support sheet,
   wherein the second surface of the support sheet is substantially impermeable to the skincare agent,
   wherein the support sheet, without the skincare agent and substance for securing the insert to skin of a user, is non-adhesive,
   wherein the support sheet is substantially non-urine absorbing, wherein the first surface of the spacing and liquid-receiving sheet is placed against the second surface of the support sheet, wherein the second surface of the spacing and liquid-receiving sheet is an exterior surface of the insert, wherein the spacing and liquid-receiving sheet is permeable to liquid in all directions, and wherein the insert is substantially non-urine absorbing.

19. An insert comprising:

a skin care agent and substance for securing the insert to skin of a user;

a support sheet; and a spacing and liquid-receiving sheet, wherein the support sheet has a first and second surface, wherein the spacing and liquid-receiving sheet has a first and second surface, wherein the skincare agent is located on the first surface of the support sheet such that the skin care agent forms a layer on the support sheet or impregnates the support sheet and completely or partially migrates into the support sheet, wherein the skincare agent covers essentially an entire area of the first surface of the support sheet, wherein the second surface of the support sheet is substantially impermeable to the skincare agent, wherein the support sheet, without the skincare agent and substance for securing the insert to skin of a user, is non-adhesive, wherein the first surface of the spacing and liquid-receiving sheet is placed against the second surface of the support sheet, wherein the second surface of the spacing and liquid-receiving sheet is an exterior surface of the insert, wherein the spacing and liquid-receiving sheet is permeable to liquid in all directions, and wherein the insert is substantially non-urine absorbing.

20. The insert of claim 1, wherein the insert is substantially non-urine absorbing such that at least the spacing and liquid-receiving sheet will not retain substantially any urine after wetting has occurred, although a few drops of liquid may be in the being held in the spacing and liquid-receiving sheet because of the capillary forces which arise.

* * * * *

UNITED STATES PATENT AND TRADEMARK OFFICE
CERTIFICATE OF CORRECTION

PATENT NO. : 7,938,812 B2  Page 1 of 1
APPLICATION NO. : 10/272934
DATED : May 10, 2011
INVENTOR(S) : Barbro Moberg-Alehammar et al.

It is certified that error appears in the above-identified patent and that said Letters Patent is hereby corrected as shown below:

Title Page,

Under (75) Inventors:

Please delete "Peter Rünnberg" and insert --Peter Rönnberg--

Please delete "Ponrus Winqvist" and insert --Pontus Winqvist--

Signed and Sealed this

Twenty-fifth Day of October, 2011

David J. Kappos
*Director of the United States Patent and Trademark Office*